US010866226B1

(12) United States Patent
Smith et al.

(10) Patent No.: US 10,866,226 B1
(45) Date of Patent: Dec. 15, 2020

(54) MULTI-POINT GROUND EMISSION SOURCE SENSOR SYSTEM

(71) Applicant: Air Stations LLC/Elevated Analytics LLC Joint Venture, Tulsa, OK (US)

(72) Inventors: Joseph D. Smith, Rolla, MO (US); Robert E. Jackson, Mapleton, UT (US); Zachary P. Smith, Broken Arrow, OK (US)

(73) Assignee: AIR STATIONS LLC/ELEVATED ANALYTICS LLC JOINT VENTURE, Tulsa, OK (US)

( * ) Notice: Subject to any disclaimer, the term of this patent is extended or adjusted under 35 U.S.C. 154(b) by 151 days.

(21) Appl. No.: 15/890,939

(22) Filed: Feb. 7, 2018

Related U.S. Application Data

(60) Provisional application No. 62/455,985, filed on Feb. 7, 2017.

(51) Int. Cl.
| | | |
|---|---|---|
| *B64C 39/02* | (2006.01) | |
| *G01N 1/22* | (2006.01) | |
| *G01N 33/00* | (2006.01) | |

(52) U.S. Cl.
CPC ....... *G01N 33/0036* (2013.01); *B64C 39/024* (2013.01); *G01N 33/0031* (2013.01); *G01N 33/0062* (2013.01); *B64C 2201/12* (2013.01); *B64C 2201/125* (2013.01);
(Continued)

(58) Field of Classification Search
CPC ........... G01N 33/0004; G01N 33/0009; G01N 33/0027; G01N 33/0031; G01N 33/0036; G01N 33/0037; G01N 33/0039; G01N 33/004; G01N 33/0042; G01N 33/0044
See application file for complete search history.

(56) References Cited

U.S. PATENT DOCUMENTS

| | | |
|---|---|---|
| 5,831,876 A | 11/1998 | Orr et al. |
| 6,085,576 A | 7/2000 | Sunshine et al. |
| 6,941,193 B2 | 9/2005 | Frecska et al. |

(Continued)

FOREIGN PATENT DOCUMENTS

| | | |
|---|---|---|
| CN | 202083808 | 12/2011 |
| CN | 103728198 | 4/2014 |

(Continued)

OTHER PUBLICATIONS

David T. Allen, Vincent M. Torres, TCEQ 2010 Flare Study Final Report, Texas Commission on Environmental Quality, The University of Texas at Austin the Center for Energy and Environmental Resources, Aug. 1, 2011.

(Continued)

*Primary Examiner* — Herbert K Roberts
(74) *Attorney, Agent, or Firm* — Head, Johnson, Kachigian & Wilkinson, PC

(57) ABSTRACT

An air quality measurement system for a plurality of adjacent ground flares. The system includes a plurality of unmanned aerial vehicles operating aerially above and around emissions from a plurality of adjacent ground flares. Sensors mounted on each of the plurality of unmanned aerial vehicles monitor atmospheric air properties. A data central processing unit receives, collects, and analyzes data from each of the sensors on each of the unmanned aerial vehicles regarding the atmospheric air properties.

12 Claims, 7 Drawing Sheets

(52) U.S. Cl.
CPC ....... *G01N 33/004* (2013.01); *G01N 33/0044* (2013.01); *G01N 33/0047* (2013.01)

(56) References Cited

U.S. PATENT DOCUMENTS

| | | | |
|---|---|---|---|
| 7,259,357 | B2 | 8/2007 | Walker |
| 7,360,461 | B2 | 4/2008 | Desrochers et al. |
| 8,765,488 | B2 | 7/2014 | Strano et al. |
| 8,955,367 | B2 | 2/2015 | Gouma et al. |
| 9,199,725 | B2 | 12/2015 | Yelland et al. |
| 9,311,805 | B2 | 4/2016 | Zishaan |
| 9,405,533 | B2 | 8/2016 | Bouzas et al. |
| 9,453,814 | B2 | 9/2016 | Tran |
| 9,536,149 | B1 | 1/2017 | Cesarano |
| 9,551,616 | B2 | 1/2017 | McQuilkin et al. |
| 2005/0139363 | A1 | 6/2005 | Thomas |
| 2005/0262943 | A1 | 12/2005 | Claydon et al. |
| 2006/0000259 | A1 | 1/2006 | Rothschild et al. |
| 2007/0005267 | A1 | 1/2007 | Li |
| 2007/0232950 | A1 | 10/2007 | West |
| 2009/0100458 | A1 | 4/2009 | Chan et al. |
| 2010/0225493 | A1 | 9/2010 | Zishaan |
| 2011/0051775 | A1 | 3/2011 | Ivanov et al. |
| 2011/0174054 | A1 | 7/2011 | Lynn |
| 2012/0015621 | A1 | 1/2012 | Cerny et al. |
| 2012/0092649 | A1* | 4/2012 | Wong ............... G01W 1/00 356/72 |
| 2012/0326093 | A1 | 12/2012 | Landorf |
| 2014/0138588 | A1 | 5/2014 | Landorf et al. |
| 2014/0315323 | A1 | 10/2014 | Pereira et al. |
| 2016/0025517 | A1 | 1/2016 | Giedd et al. |
| 2016/0284221 | A1* | 9/2016 | Hinkle ............... B64C 39/024 |
| 2017/0016850 | A1 | 1/2017 | Tran |
| 2017/0038326 | A1* | 2/2017 | Motayed ............ G01N 33/0054 |
| 2017/0168487 | A1* | 6/2017 | Mantripragada ...... G01N 29/02 |
| 2017/0235316 | A1* | 8/2017 | Shattil ............... H04B 7/18504 701/3 |

FOREIGN PATENT DOCUMENTS

| | | |
|---|---|---|
| CN | 104458905 | 3/2015 |
| CN | 104583764 | 4/2015 |
| CN | 104713922 | 6/2015 |
| CN | 204557260 | 8/2015 |
| CN | 204719251 | 10/2015 |
| CN | 105051658 | 11/2015 |
| CN | 204901580 U | 12/2015 |
| CN | 204964476 | 1/2016 |
| CN | 106168617 | 11/2016 |
| EP | 527307 | 2/1993 |
| EP | 2048854 | 4/2009 |
| EP | 2304427 | 4/2011 |
| EP | 2699888 | 2/2014 |
| EP | 3092540 | 11/2016 |
| EP | 2761285 | 2/2017 |
| EP | 3183722 | 6/2017 |
| KR | 1020110077040 | 7/2011 |
| KR | 1020150112118 | 10/2015 |
| NZ | 566000 | 4/2011 |
| WO | 2009013508 | 1/2009 |
| WO | 2010013023 | 2/2010 |
| WO | 2010037425 | 4/2010 |
| WO | 2012023136 | 2/2012 |
| WO | 2012177975 | 12/2012 |
| WO | 2013112287 | 8/2013 |
| WO | 2014081331 | 5/2014 |
| WO | 2016145300 | 9/2016 |
| WO | 2016147098 | 9/2016 |
| WO | 2017068499 | 4/2017 |

OTHER PUBLICATIONS

Kelsey D. Atherton, NASA Now Has a Drone That Can Sniff Out Dangerous Gas Leaks, Popular Science, Mar. 30, 2016.
Black Swift Technologies, Commercial & Scientific Unmanned Aircraft, http://blackswifttech.com/, 2017.
Christophe Buchler, Magali Rollin, User-Friendly Composites That Take the Heat, JEC Magazine, Nov.-Dec. 2009, p. 33-35, No. 53.
Shay Castle, Boulder's Black Swift Wins NASA Deal for Drone-Based Volcano Tracking, Boulder Daily Camera, May 3, 2017.
Dennis Fandrich, Mark Iden, Drones with Innovative Gas Detection Sensors Usher in a New Pipeline Inspection Era, Pipeline Technology Journal, Mar. 30, 2016.
Luke Geiver, GE Unveils Drone, Sensor Package Aimed at Detecting Fugitive Gas, UAS Magazine, Oct. 12, 2016.
Dr. Felipe Gonzalez, Miguel A. Alvarado Molina, Tommaso Villa, UAVs for Gas Plume and Ultrafine Particles Monitoring, Mining and Energy in 2025 & Beyond, May 26, 2016.
GPS World Staff, Inspector Gadget: Drones Could Solve Gas-Leak Detection Issue, GPS World, Mar. 5, 2016.
Matthew R. Johnson, Robin W. Devillers, Kevin A. Thomson, Quantitative Field Measurement of Soot Emission from a Large Gas Flare Using Sky-LOSA, Environmental Science and Technology, 2011, vol. 45. p. 345-350.
Matthew R. Johnson, Robin W. Devillers, Chen Yang, Keven A. Thomson, Sky-Scattered Solar Radiation Based Plume Transmissivity Measurement to Quantify Soot Emissions from Flares, Enviromental Science and Technology, Sep. 23, 2010, vol. 44, No. 21, p. 8196-8202.
R. Colin Johnson, Gas Sensors Penetrate Smartphones, EE Times, Nov. 5, 2015, AspenCore.
Marc McDaniel, Flare Efficiency Study, Engineering-Science, Inc., Jul. 1983.
James D.N. McEwen, Matthew R. Johnson, Black Carbon Particulate Matter Emission Factors for Buoyancy-Driven Associated Gas Flares, Journal of the Air & Waste Management Association, Jan. 20, 2012.
Mariella Moon, GE Made an Oilfield Drone That Can Sniff Out Gas Leaks, Engadget, Oct. 9, 2016.
Rhett Morgan, Zeeco Calls Its New Direct Flare-Monitoring Technology a Game-Changer, Tulsa World, Jul. 28, 2017.
NASA, Carbon Nanotube Sensors for Gas Detection, Ames Technology Capabilities and Facilities, NASA.gov, Jul. 18, 2016.
NASA, NASA Flies Dragon Eye Unmanned Aircraft Into Volcanic Plume, www.nasa.gov, Apr. 2, 2013.
NASA, Mini NASA Methane Sensor Makes Successful Flight Test, Jet Propulsion Laboratory California Institute of Technology, Mar. 28, 2016.
National Aeronautics and Space Administratioin (NASA), NASA Ames Scientist Develops Cell Phone Chemical Sensor, NASA.gov, Oct. 30, 2009.
Mark Scott, Energy Giants Turn to Drones and Sensors in New Embrace of the Digital World, The New York Times, Nov. 3, 2016, The New York Times Company.
URS Corporation, Passive FTIR Phase I Testing of Simulated and Controlled Flare Systems Final Report, Texas Commission on Environmental Quality, Jun. 2004.
U.S. EPA Office of Air Quality Planning and Standards (OAQPS), Parameters for Properly Designed and Operated Flares, Report for Flare Review Panel, Apr. 2012.
VTT Technical Research Centre of Finland, Scientists Developed a Miniature Gas Sensor for Mobile Devices—Applications from Monitoring Air Quality to Healthcare & Wellness, vttresearch.com, Aug. 13, 2015.

* cited by examiner

MULTI-POINT GROUND EMISSION SOURCE SENSOR SYSTEM

CROSS-REFERENCE

This application claims priority to and the benefit of U.S. Provisional Patent Application Ser. No. 62/455,985, filed Feb. 7, 2017, which is incorporated herein in its entirety by reference.

BACKGROUND OF THE INVENTION

Field of the Invention

The present invention is directed to an air quality measurement system to assess atmospheric air quality using a plurality of unmanned aerial vehicles, each having sensors to monitor a plurality of adjacent ground emission sources, such as ground flares, wherein data from multiple movable sensors is combined to both define and predict movement of emissions from multi-point ground emission sources.

Description of the Related Art

The petrochemical and chemical industries, among other industrial and commercial sources, routinely use gas flares to dispose of large amounts of flammable hydrocarbon gases produced in various manufacturing and industrial processes. In addition, landfill will often include gas flares for methane and other gas emissions.

It is desirable to identify and quantify emissions from manufacturing, industrial and other sources. Flare performance depends on mixing flare gases with surrounding air to ensure complete and efficient combustion of all waste gases. When these gases burn above the flare tip, depending on the combustion conditions (i.e., sufficient mixing to ensure proper combustion) toxic chemicals can be emitted [1]. The resulting plume evolves from the visible flame above the flare tip. Due to the temperature difference between the hot combustion gases in the combustion zone above the flare tip and the surrounding air at ambient temperature, buoyance causes the plume to rise and expand as it mixes with air. Plume momentum carries the combustion effluent upward and away from the flare tip to a point where the atmospheric conditions control the plume's trajectory. Flow from the flare stack quickly dissipates as it mixes and entrains ambient air. External wind also causes the flare plume to lose vertical momentum and bend over due to the horizontal momentum of the wind. Wind speeds usually increase with elevation, so plumes that form higher above the ground transition to horizontal flows more quickly. Wind also reduces plume buoyancy by increasing the entrainment rate of cooler surrounding air into the plume. The greater the wind speed, the faster the plume mixes with the ambient air and cools, thus losing its buoyancy and reducing how high it rises above the flare exit. The plume shape and size are strongly affected by wind speed, which distorts the plume as it moves away from the flare stack. See FIG. 1 which illustrates emissions from a flare stack with three different wind speeds. As the plume rises and expands, pollutants disperse into the surrounding atmosphere as they are transported downwind in the plume and may eventually reach ground level where they can be quantified using standard analytical equipment. To assess potential health risks related to emission levels at ground level downwind of a flare, plume dispersion analysis is routinely performed.

Basic plume dispersion analysis considers emissions coming from a single point with plume dispersion being subject to atmospheric stability and wind conditions. See FIG. 2 which illustrates charts of Gaussian analysis. This type of analysis normally relies on Gaussian dispersion [2]:

$$\chi = \frac{Q}{2\pi\sigma_y\sigma_z u} e^{-\frac{1}{2}\left(\frac{y}{\sigma_y}\right)^2} \left\{ e^{-\frac{1}{2}\left(\frac{z-H}{\sigma_z}\right)^2} + e^{-\frac{1}{2}\left(\frac{z+H}{\sigma_z}\right)^2} \right\} \quad \text{Equation (1)}$$

where:
 $\chi$=ground level pollutant concentration (g/m$^3$)
 Q=mass emitted per unit time
 $\sigma_y$=standard deviation of pollutant concentration in y (horizontal) direction
 $\sigma_z$=standard deviation of pollutant concentration in z (vertical) direction
 u=wind speed
 y=distance in horizontal direction
 z=distance in vertical direction
 H=effective stack height This analysis assumes: 1) relatively flat surface along the plume path; 2) the plume is reflected by the ground; 3) a constant plume emission rate; and 4) a uniform wind speed and direction. Applying Eq. 1 to dispersion of flare plumes, one must estimate plume rise which relates "buoyancy flux" and wind speed to plume rise [3]:

$$\Delta h = \frac{1.6 F_b^{1/3}(x)^{2/3}}{\bar{u}} \quad \text{Equation (2)}$$

where $\bar{u}$ is the average wind speed, x is the downwind distance from the plume origin and $F_b$ is the "buoyancy flux" factor defined as:

$$F_b = g v_g \frac{d_s^2}{4}\left(\frac{T_g - T_a}{T_a}\right) \quad \text{Equation (3)}$$

with g being the gravity acceleration, $v_g$ as the flare gas exit velocity, $T_g$ as the plume gas temperature and $T_a$ as the ambient air temperature. While Eq. 2 estimates plume rise due to buoyancy, some plumes are momentum dominated (i.e., high tip velocity from elevated flares) so plume rise is calculated as:

$$\Delta h = \left(\frac{3 F_m x}{\beta_j^2 \bar{u}^2}\right)^{1/3} \quad \text{Equation (4)}$$

where $\beta_j$ is the jet entrainment coefficient:

$$\beta_j = \frac{1}{3} + \frac{\bar{u}}{v_g} \quad \text{Equation (5)}$$

and the "momentum flux" parameter is defined as:

$$F_m = \frac{v_g^2 d_s^2}{4}\left(\frac{T_a}{T_g}\right) \quad \text{Equation (6)}$$

with $v_g$ as the flare exit gas velocity and $d_s$ as the flare exit diameter ($T_a$ and $T_g$ defined as before).

Plume transport is also affected by nearby structures and local topology, which may lead to higher than estimated surface concentrations using the basic one-dimensional (1-D) plume dispersion analysis, which considers an imaginary centerline along the plume trajectory where maximum concentration exists and assumes uniform distribution from this centerline path. This dispersion analysis relies on two parameters (i.e. $\sigma_y$ for horizontal dispersion and $\sigma_z$ for vertical dispersion) to estimate emission levels at ground level assuming time-averaged atmospheric temperature and wind speed/direction. Although more complex plume models developed by the U.S. Environmental Protection Agency [4] take additional factors into account, predicted ground levels of harmful chemicals are not adequate to accurately quantify ground level emissions from a single flare, which must be done using analytic equipment and well-established test procedures to quantify health risk.

One example of using an unmanned aerial vehicle to measure flare emissions from a single flare is shown in Applicant's co-pending application Ser. No. 15/794,064, titled Air Quality Measurement System, which is incorporated in its entirety by reference.

The present invention extends the concepts of the previous invention in Applicant's co-pending application consisting of sensors that can determine various properties in gases and liquids [11], [12], [13], [14] mounted on a single UAV to monitor emissions including (but not limited to) CO, $CO_2$, $H_2O$, $CH_4$, NOx, SOX, and other hydrocarbon gases contained in a typical plume produced by the combustion zone above a single non-assisted or assigned flare tip.

Compared to a single elevated flare, a Multi-Point Ground Flare (MPGF) is comprised of multiple flare burners arranged together in rows or other patterns and operated stage-wise to burn increasing amounts of flare gas. FIG. 3 illustrates a non-limiting example of a typical burner tip flare layout in a multi-point ground flare. The complex plume coming from a MPGF is formed by plumes from individual flare burners included in a MPGF (see FIG. 3). These plumes coalesce and merge into a large composite plume as shown in FIG. 4. Neither the one-dimensional (1-D) Gaussian dispersion analysis described earlier nor the more complex EPA plume models are able to capture the complex dynamics associated with this type of composite plume. Also, single point measurement devices routinely used to measure flare emissions cannot quantify flare emissions from an MPGF given the size and complexity of the composite plume emitted from a MPGF. And, compared to an elevated flare which is located high above the ground so any emissions are dispersed over a larger area, emissions from a MPGF, located near the ground, reach the ground much sooner. Thus, known plume dispersion analysis is not sufficient to estimate ground level emission levels from an MPGF. Also, typical analytical test equipment designed and applied to measure ground level emissions from a single flare tip cannot efficiently nor accurately capture the continuous emission levels from a MPGF.

The following discussion illustrates the value of the present invention, having multiple sensors organized in a sensor array to better quantify ground level flare dispersion, and to demonstrate the value of having a system of mobile sensors mounted on UAVs which can freely move and record gas concentrations, gas temperature, and humidity as a function of location, elevation and time.

Measuring the temperature and species concentrations of toxic emissions contained in the plume emanating from a large multi-point ground emission source into the surrounding environment has never been reported in the literature due to the scale of such a measurement. Previous work has focused on characterizing the performance of single point elevated flares in terms of combustion efficiency and emissions (i.e., CO, $CH_4$, unburnt hydrocarbons, and soot). Flare testing sponsored by the Chemical Manufacturers Association (CMA) in 1983 [5] was the first well designed experiment aimed at measuring soot, CO and unburned hydrocarbon emissions from non-assisted utility flare tips and steam and air assisted flare tip using extractive sampling techniques together with a gas chromatograph. A more recent study sponsored by the Texas Commission on Environmental Quality (TCEQ) [6] conducted in 2010 at the John Zink flare test facility reproduced the results collected using extractive testing and also extended the work by applying Open-Path Fourier Transform Infra-Red Spectroscopy (OPFTIR) to quantify flare performance. Flare testing has also focused on Black Carbon (BC) emissions conducted by Johnson et al. [7] [8] [9]. Recent work has resulted in the development of the SKY-LOSA optical technique for measuring BC [8], [9], the passive FTIR (PFTIR) technique [10], and a unique sample probe system developed by Aerodyne Research, Inc., (ARI) used in the TCEQ study [6]. All previous tests focused only on single point non-assisted and assisted flare tips and were limited to collecting samples from a single region above the flare combustion zone. The collected samples represented temporally and spatially averaged gas concentrations emitted from the flare. Although this early work provided useful information that allowed flare vendors, flare operators and the regulatory agency to quantify flare emissions, averaged results cannot provide detailed understanding of the turbulent mixing and heat transfer occurring inside a complex flare plume as a function of time and position, nor did they quantify flare emission levels in the plume as the plume dispersed downwind from the combustion zone above the flare tip. The current state of the art in measuring flare emissions relies on local fixed location measurements of the plume coming from large operating industrial flares. Although the PFLIR and SKY-LOSA techniques offer some hope of accomplishing this for single point flares, they are not designed nor applicable to multi-point ground flares (MPGF). Also, the initial capital costs for this type of equipment and the setup and operation costs of conducting routine on-site tests of large operating flare is too prohibitive for routine use. The current invention provides an affordable mechanism available to measure a wide range of emissions, as well as the local temperature and relative humidity, from MPGFs in a comparatively short time.

Being able to monitor the dispersion of the gases from several hundred flare tips operating simultaneously in a MPGF instead of relying on one or two sampling locations downstream of an operating MPGF can provide valuable insight into the dispersion of the complex flare plume and provide more accurate indications of the impact these flares might have on plant personnel and surrounding communities.

Based on the foregoing, it is desirable to provide a system capable of identifying and quantifying combustion effluent emissions from multiple ground flares in industrial and commercial sources.

It is further desirable to provide a system to measure atmospheric air quality to monitor atmospheric properties at various locations, elevations, and times from multiple ground flares.

It is further desirable to provide a system to utilize atmospheric air measurements to predict future movement or dispersion of combustion effluent emissions from multiple ground flares.

SUMMARY OF THE INVENTION

In general, the present invention is directed to an air quality measurement system for multiple ground emission sources. A plurality of sensors capable of measuring temperatures, relative humidity, as well as species concentrations of key compounds, are mounted on each of a series of unmanned aerial vehicles which operate concurrently in a controllable aerial formation to surround a large area where multiple combustion devices are burning flammable hydrocarbon gases—referred to as a multi-point ground flare.

Unmanned aerial vehicles (UAV) of the present invention may take different forms and include a communication transmitter to send measured properties to a central processing computer and an antenna by which its position is determined and controlled from a ground-based control computer. The UAVs are constructed of high temperature glass-ceramic matrices and inorganic polymers which are temperature and chemical resistant.

The present invention includes using a fleet of small unmanned aerial vehicles (UAV) operated together strategically located around the multi-point ground flare (MPGF) in a "swarm" configuration with data collected by wireless sensors mounted on each UAV. The data from each UAV is transmitted to a central processing unit device that records, analyzes and displays a three-dimensional image of the spatially accurate time-varying plume emanating from the MPGF.

A plurality of sensors is mounted on a rigid substrate onboard each UAV. A power source, also mounted on the UAV, provides substantially constant current to the electrically interconnected sensors. The resistance or capacitance of the electrically interconnected sensors is correlated to temperature and/or pressure. Additionally, and separately, relative humidity and gas temperature measurements are obtained. In addition, sensors capable of measuring gas species are mounted on the UAV.

The data gathered is sent from each UAV and transmitted to a central processing unit. The data is recorded, analyzed, and displayed in a three-dimensional image.

DETAILED DESCRIPTION OF THE INVENTION

The embodiments discussed herein are merely illustrative of specific manners in which to make and use the invention and are not to be interpreted as limiting the scope.

While the invention has been described with a certain degree of particularity, it is to be noted that many modifications may be made in the details of the invention's construction and the arrangement of its components without departing from the scope of this disclosure. It is understood that the invention is not limited to the embodiments set forth herein for purposes of exemplification.

Figure 1:
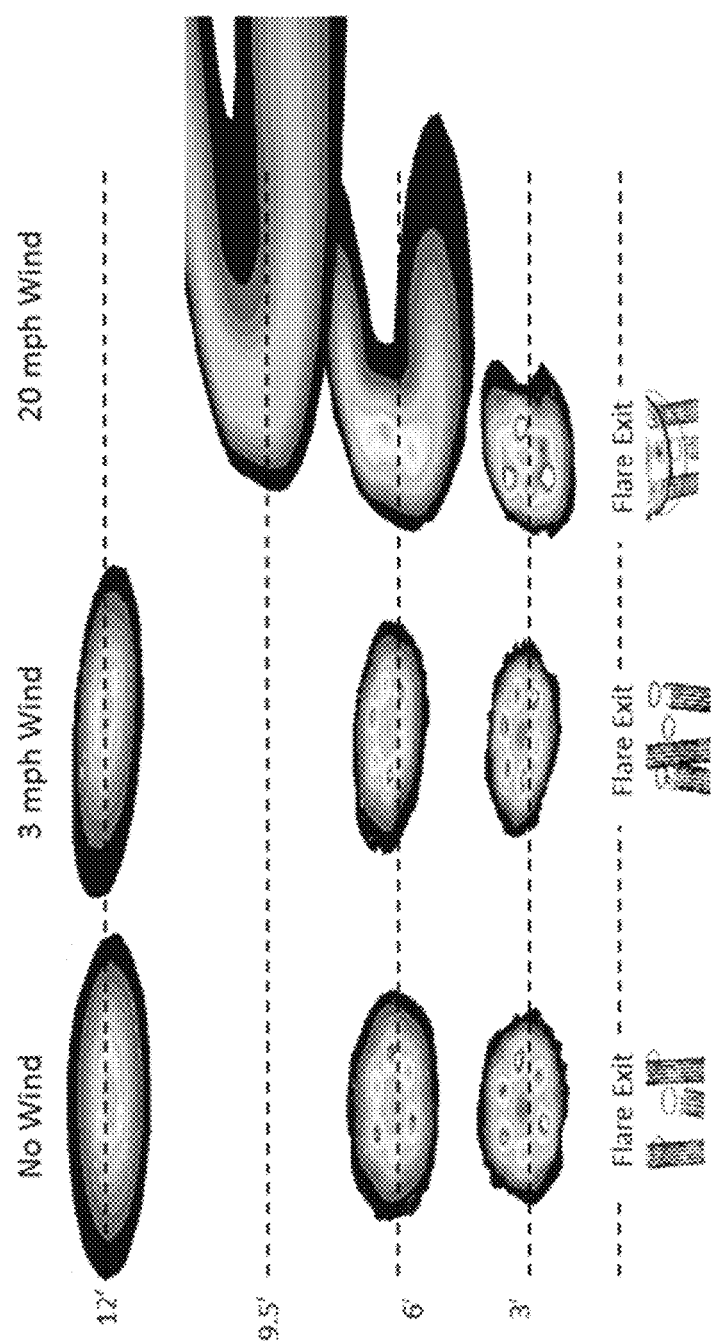
FIG. 1 illustrates emissions plumes from a flare stack showing three different wind conditions and various elevations.

Referring to the drawings in detail, FIG. 1 illustrates examples of emission plumes from a flare stack showing three different wind conditions and various elevations. Plume momentum carries the combustion effluent upward and away from the flare tip. External wind causes the flare plume to lose vertical momentum and also bend to horizontal momentum of the wind. Wind effect on a plume from a single elevated air-assisted gas flare shows the shape of the resulting plume coming from the flare tip at increasing wind speeds. For example, for a 20 mile per hour wind, the plume forms a familiar horseshoe shape with the downwind centerline of the plume having low oxygen concentrations resulting in unburnt hydrocarbon (and soot).

As the plume rises and expands, gaseous emission pollutants disperse into the surrounding atmosphere as they are transported downwind in the plume and may eventually reach ground level where they could be quantified using standard analytical equipment on the ground.

The system can track a flare plume to measure emissions from the flare which are carried in the flare plume downwind of the flare using advanced sensor technology, such as described herein. Plume tracking is facilitated using artificial intelligence employing self-training techniques such as neural networks. The plume tracking system is based on two-parameter data which includes measured gas temperature and relative humidity, known to be highest inside a plume compared to surrounding ambient air, to quantify the plume. As the air temperature and moisture content of the air is measured, the UAV is directed to move into the direction of increasing levels. An advanced search algorithm (e.g., a combinatorial search) efficiently finds the plume location by reducing the effective search space using heuristics to find the plume location. The search algorithm uses predicted plume location from computational fluid dynamics analysis of the flare subject to ambient conditions to help establish the general plume location as an initial starting location that the algorithm uses and updates the plume location using measured local air temperature and moisture content to optimize and track plume location. Output from the search algorithm is used by the drone GPS algorithm to continuously adjust the UAV position to ensure it remains inside the plume. When the UAV exits the plume, measured air temperature and moisture content will decrease and the search algorithm will instruct the UAV to move in an optimal direction that moves it back into the plume. When the UAV is within the plume, air temperature and moisture content is continuously monitored and reported to ground-based monitoring equipment to show plume as an iso-surface image. This visual image helps the operator monitor UAV plume tracking to provide correction as, or if, necessary.

Figure 2:
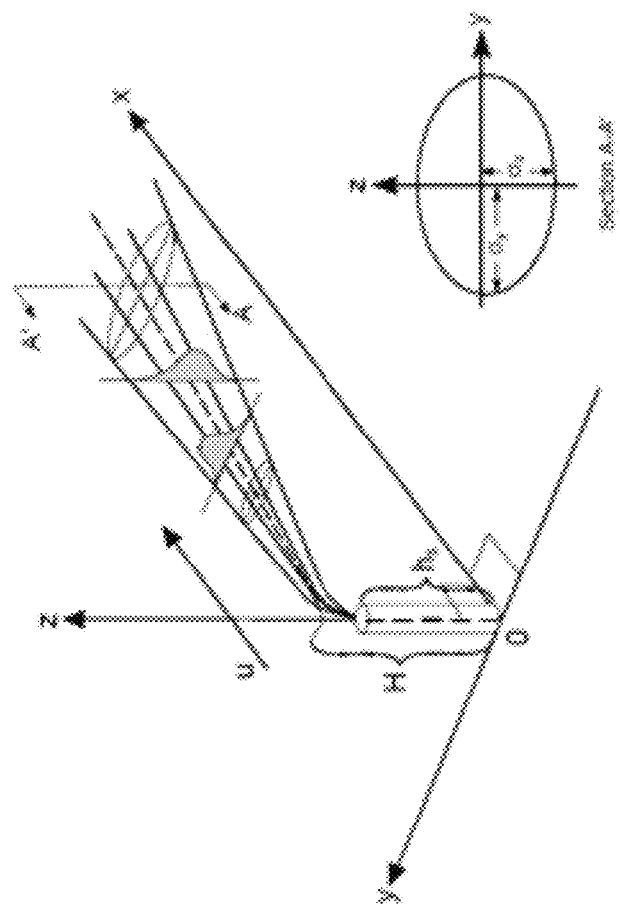
FIG. 2 illustrates two separate charts showing standard plume dispersion analysis based on standard Gaussian dispersion analysis.
Figure 2:
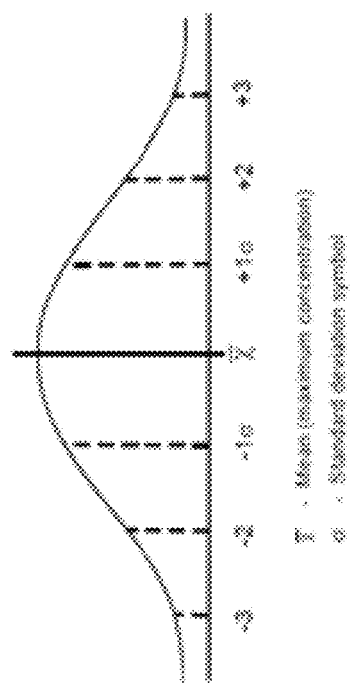

FIG. 2 illustrates two separate charts showing standard plume dispersion analysis based on standard Gaussian dispersion analysis. The standard analysis does not account for the variations caused by the interactions of multiple plumes.

Figure 3:
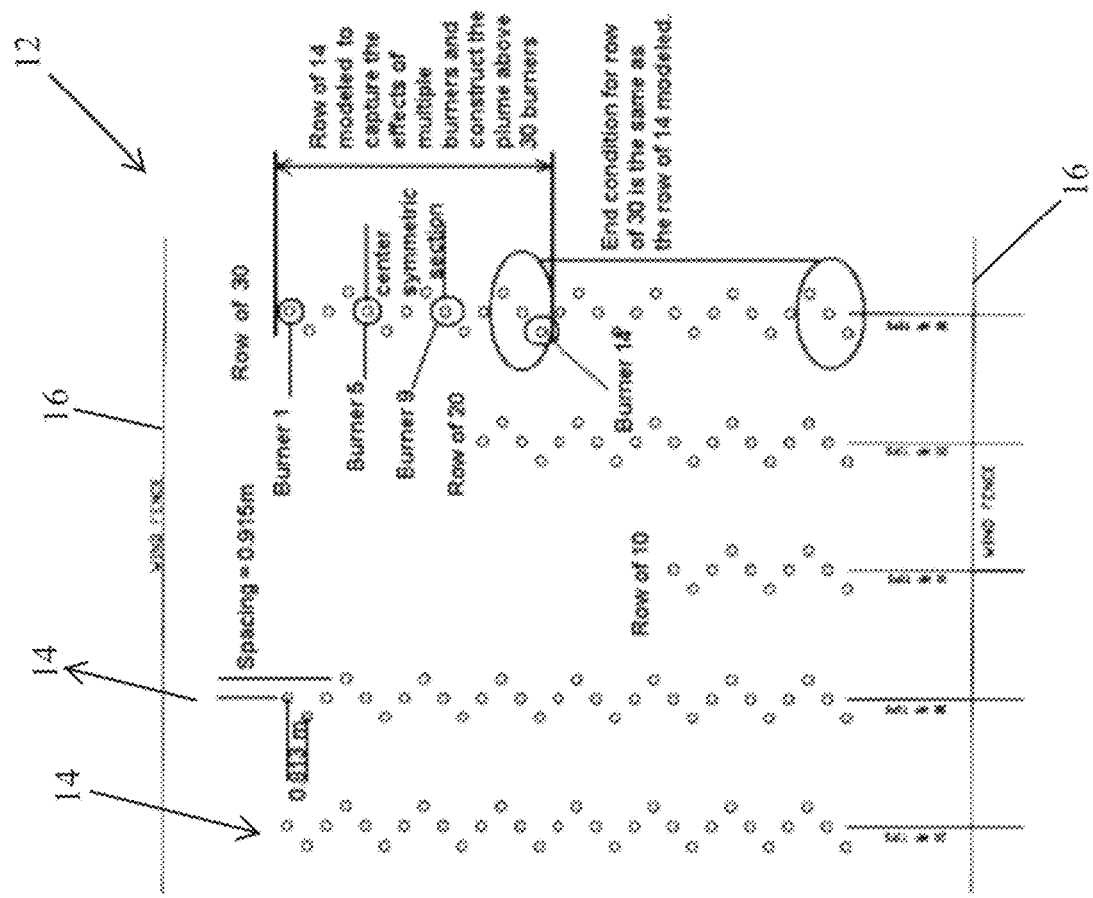
FIG. 3 illustrates a top view of a multi-point ground flare (MPGF) array.

FIG. 3 illustrates a non-limiting example of a multi-point ground flare (MPGF) array 12. A large number of individual flare burners are arranged in multiple rows 14. In some cases, hundreds of flare burners are employed. A wind fence 16 may surround the entire multi-point ground flare array 12 so that the effect of wind is more pronounced above the level of the fence line. A multi-point ground flare array 12 may contain up to hundreds of flare burners which are arranged in multiple rows. Several of the rows may be organized into a stage or stages of an array. One or more of the stages may be operated at any one time. In one non-limiting example, when the multi-point ground flare array is operated, flare gas flow is sent to the initial stages, with subsequent stages used to burn more and more flare gas.

Interaction between the flare burners and the flames therefrom forming above each of the flare burners arranged in the multi-point ground flare creates non-standard operation and leads to unexpected flare performance and unexpected combustion effluent plumes.

Figure 4:
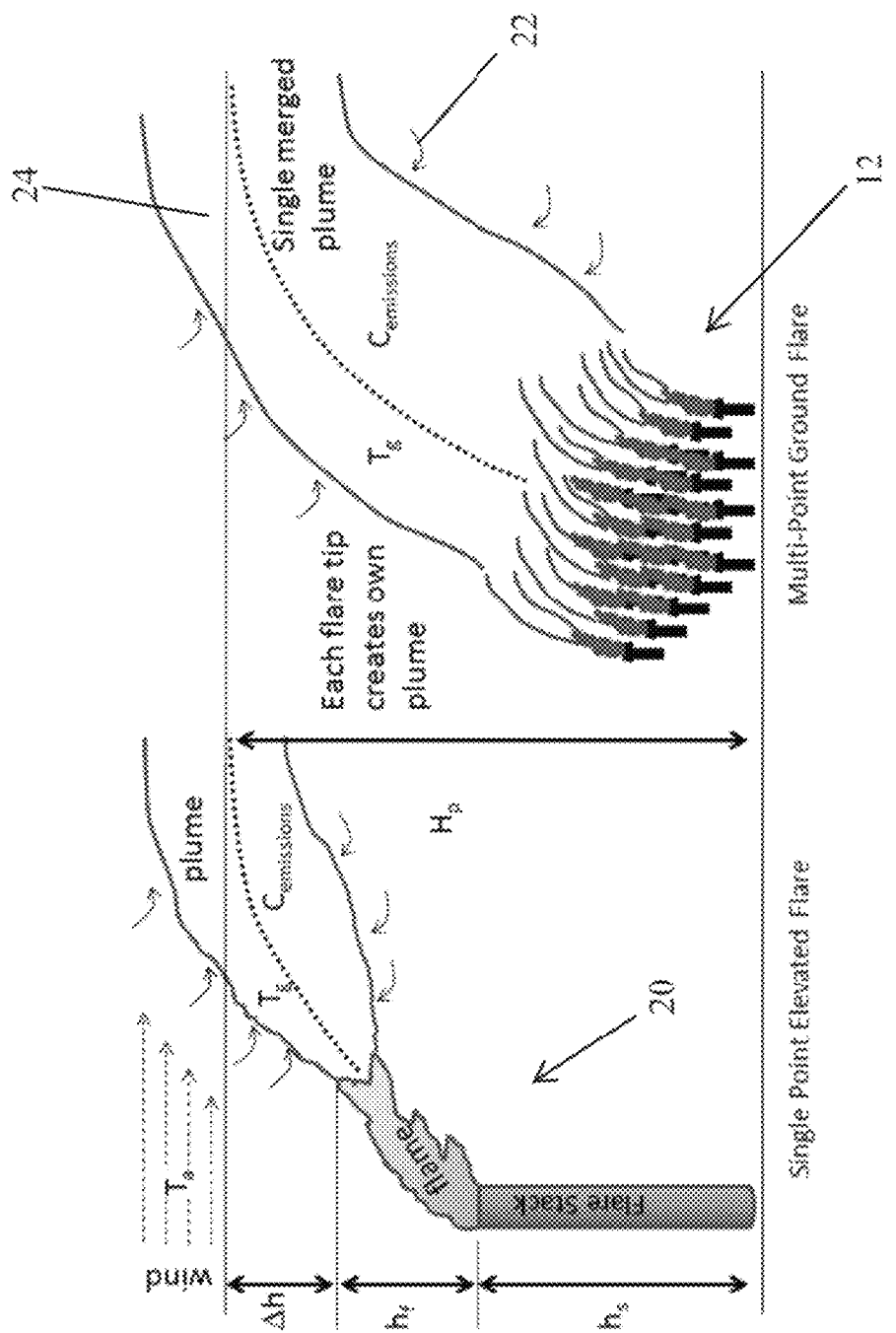
FIG. 4 shows a diagrammatic illustration of emissions from a single-point elevated flare versus a multi-point ground flare array.

FIG. 4 shows a diagrammatic illustration of a single point elevated flare 20 versus a multi-point ground flare array 12. The wind forces are illustrated by arrows 22. The individual flares and combustion effluent from each burner are merged into a complex combustion effluent plume 24. The complex plume 24 transports partially burned flare gas or incomplete combustion byproducts generated during the multi-point ground flare operation. The complex nature of the plume 24 may be observed.

Figure 5:
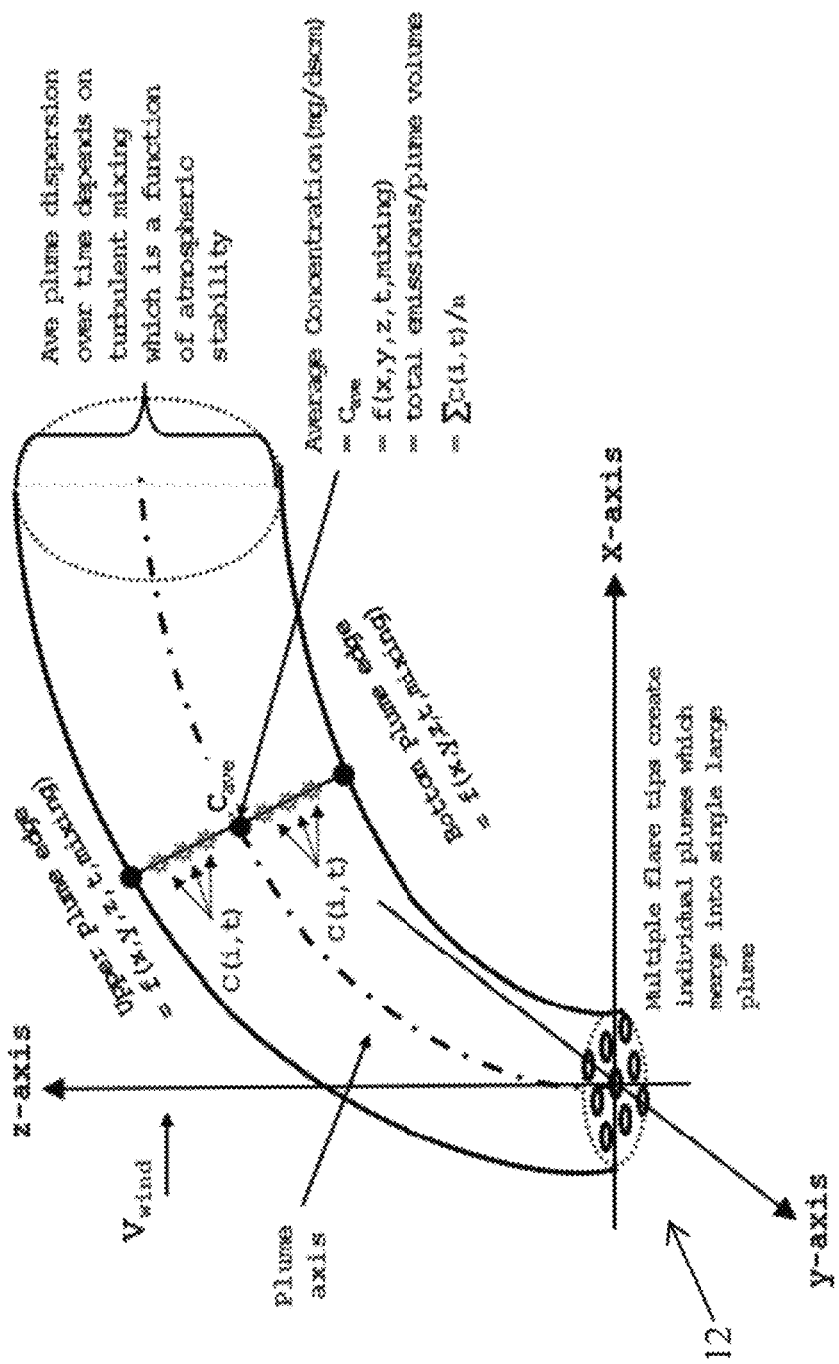
FIG. 5 illustrates a graph of an analytical model applying standard Gaussian distribution theory to a multi-point ground flare plume dispersion.

FIG. 5 illustrates a graph of an analytical model applying standard Gaussian distribution theory to multi-point ground flare plume dispersion. Multiple flare tips of the array 12 create individual plumes which thereafter merge into a single large complex combustion effluent plume.

Figure 6:
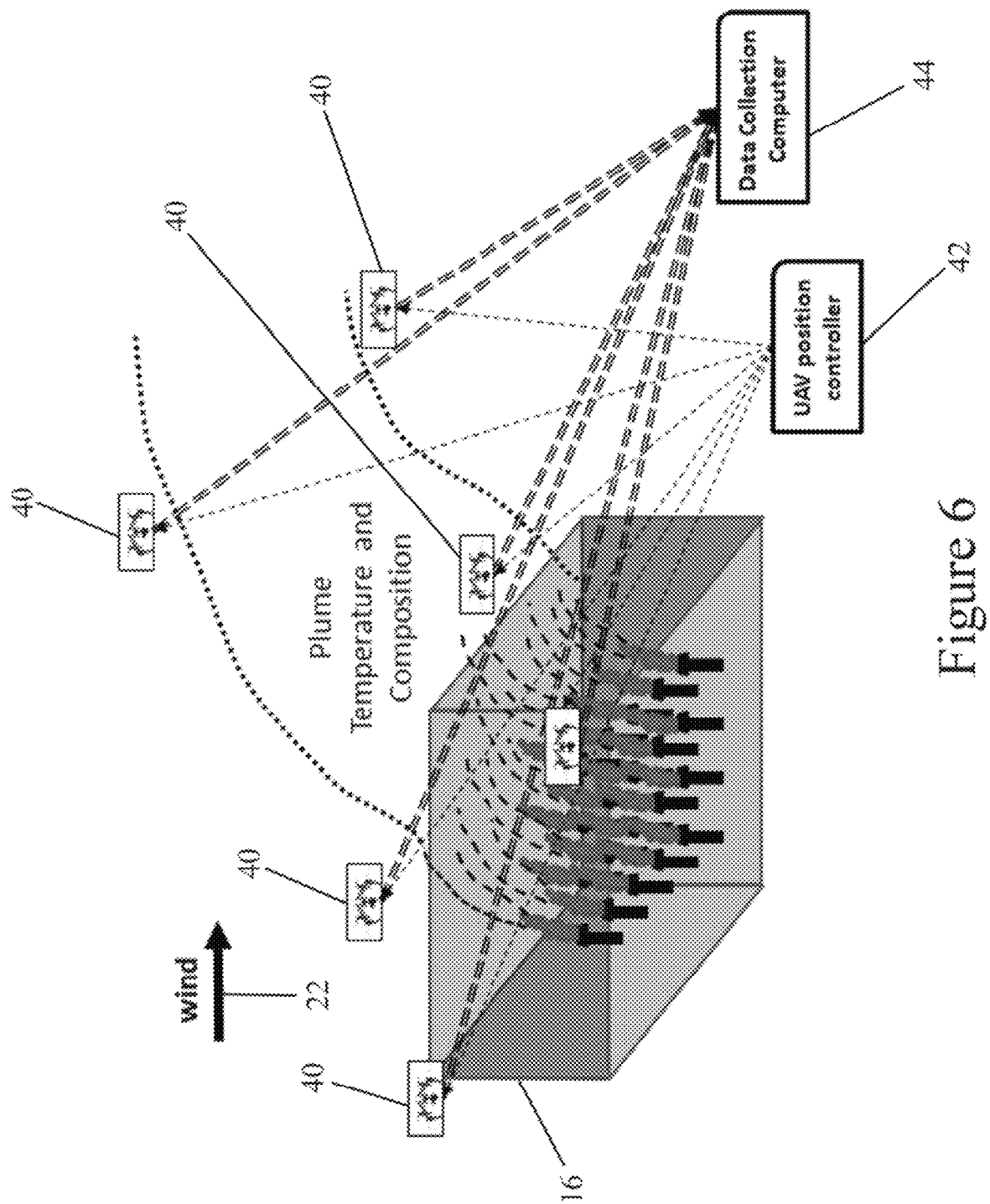
FIG. 6 illustrates a diagrammatic example of a multi-point ground flare system of the present invention.

FIG. 6 illustrates a diagrammatic example of the multi-point ground flare sensor system of the present invention.

A wind fence 16 is shown surrounding the multiple flare array 12.

A plurality of unmanned aerial vehicles (UAV) 40 are deployed above and around the multi-point ground flare array 12. The UAVs are constructed of high temperature glass-ceramic matrices and inorganic polymers which are temperature and chemical resistant. Each of the unmanned aerial vehicles is capable of flying around and into a plume where the local gas temperature does not exceed 800K.

The combustion effluent plume includes various gas species, as well as water vapor and carbon dioxide.

Each of the unmanned aerial vehicles 40 is in wireless communication with a position controller 42 on or near the ground. Each UAV includes a transmitter and receiver. Each UAV uses the plume tracking algorithm described earlier to remain inside the plume in relation to each other to fully map emissions carried from the flare tips in the plume to the ambient surroundings. The position controller 42 includes a central processing unit and a database and a transmitter and receiver to communicate with each of the unmanned aerial vehicles. Each of the unmanned aerial vehicles is mobile and can freely be deployed to a desired location.

Each unmanned aerial vehicle includes a plurality of electrically interconnected sensors.

Sensors and transducers comprising a thin, electronically "active" sensing layer within a dielectric and/or metallic layered structure may be utilized. The electronic resistance of the active sensing layer is measured during a change in the sensor environment. As the sensors come into contact with different concentrations of gases, primarily in, but not limited to, an air matrix, the electronic resistance of the sensing layer changes. This change is proportional to the concentration of analyte gas. The sensing layer thickness are of the order of nanometer scale which provides for rapid response in the sub-one second range. These sensors are also capable of discriminating between multiple gases on the same sensing layer. This allows for a number of specific application areas for environmental sensing.

In one non-limiting example, the sensors may also include Micro-Electro-Mechanical-Systems (MEMS) which use the mechanical changes in micro-scale or nano-scale devices to sense the gas concentrations. The mechanical properties of the MEMS sensor changes as gases are absorb onto the surface and the change is proportional to the concentration of the gas. These MEMS type sensor also have rapid response, can discriminate between multiple gases and can accurately sense multiple gases with the same MEMS sensing device. Novel transducers can be incorporated into sensors, as well as methods of using those transducers to detect the existence of a certain condition, such as a change in temperature or the presence of an analyte. Typical analytes that might be detected include those selected from the group consisting of humidity, gas, airflow, volatile organic compounds (VOCs such as amides, aldehydes, ethers, ketones, esters, and alcohols), and combinations of the foregoing. Advantageously, the present invention is particularly useful for detecting VOCs.

The unmanned aerial vehicles 40 each gather information on various gas species including volatile organic compounds. Sensor information from each of the unmanned aerial vehicles is transmitted wirelessly back to a ground-based data collection center computer 44, along with time and location information. The data collection computer collects and organizes the data in such a way to allow the data to be used to quantify instantaneous performance of the multi-point ground flare 12. The data collection computer 44 includes a central processing unit and a database, as well as a transmitter and receiver.

It will be understood that the position controller 42 and data collection computer 44 may be operated together or in conjunction with each other.

Figure 7:
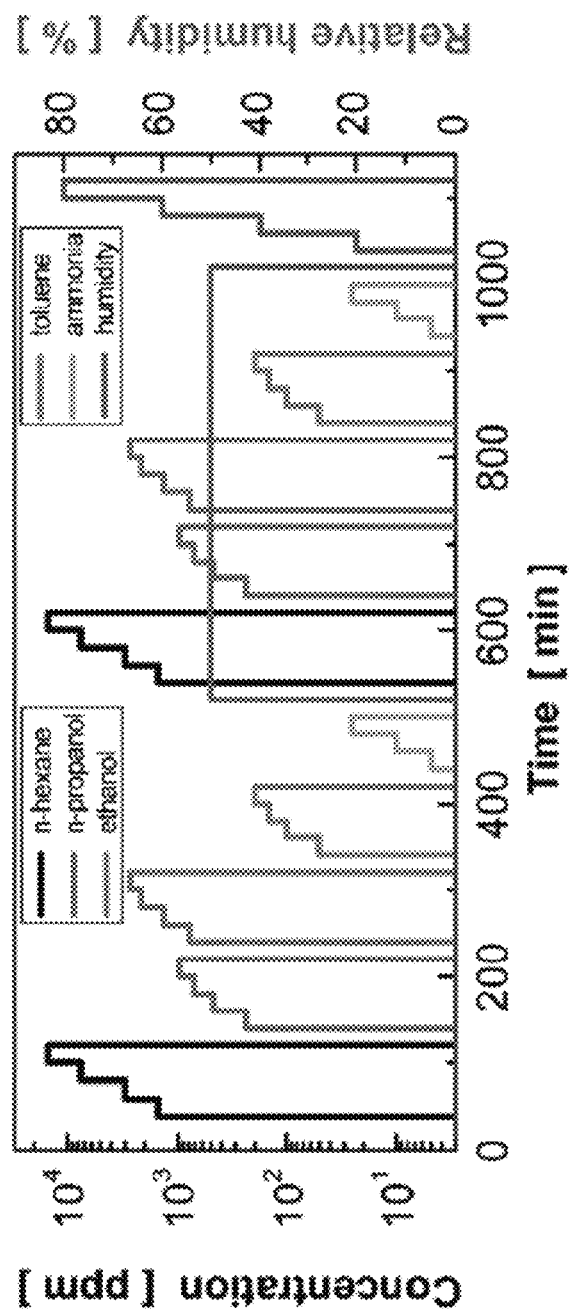
FIG. 7 is a chart or graph illustrating analysis of various measurements taken by sensors of a multi-point ground flare plume.

FIG. 7 is a chart or graph illustrating analysis of measurements taken by the sensors on the unmanned aerial vehicles of a multi-point ground flare plume. The X axis illustrates time in minutes. The left Y axis indicates concentrations in parts per million of various compositions, while the right Y axis illustrates atmospheric relative humidity. Various chemical compounds or compositions may be monitored including, but not limited to, n-hexane, n-propanol, ethanol, toluene, and ammonia, as well as relative humidity. Species concentrations measured by the sensors are plotted as shown in the drawing. Based on the response of the sensor, concentrations for the gases being measured by the sensor are determined from previously defined algorithms in the microcontroller and these concentrations, along with temperature, relative humidity, barometric pressure and location data are then outputted via wireless communication to the data collection computer 44.

Multiple UAVs 40 with sensor systems can be collecting data simultaneously at different physical locations and transmitting their data to the same or to multiple data collection computers 44. The UAVs 40 may be synchronized via special software algorithms to take data throughout the flare plume and surrounding area, providing a complete mapped dataset for the entire MPGF, its plume, and the surrounding area. This dataset can be used to investigate properties in or about the MPGF plume. For example, the dataset may be used to show a surface contour plot of a selected species, temperature, relative humidity, or other parameter around the area of the multi-point ground flare array as a function of time during the test. Similarly, contour plots on a planar slice through the plume can be used to show properties of the plume relative to ambient conditions outside the plume.

Information about the location of a combustion effluent plume and its predicted path may be determined. Concentrations of gases (or other parameters) inside the plume may be integrated over space to get special averaged values. Concentrations of gases (or other parameters) may also be averaged over time.

The data gathered may be recorded, analyzed, and displayed in a three-dimensional image. For example, an iso-surface of carbon dioxide at a specific level (e.g., 10%) may be plotted showing the general shape of the plume in three dimensions. This data may be combined with detailed three-dimensional topographical images of the flare and surrounding structures and landscape to provide insight into the impacts of the flare on its surroundings.

This information can be further analyzed or transmitted to a plant control room, monitored by plant operators to ensure safe conditions for employees, and transmitted and stored to confirm compliance with various regulatory measures.

Whereas, the invention has been described in relation to the drawings attached hereto, it should be understood that other and further modifications, apart from those shown or suggested herein, may be made within the scope of this invention.

BIBLIOGRAPHY

[1] N. Soelberg and J. Pohl, "Evaluation of the Efficiency of Industrial Flares: Flare Head Design and Gas Composition," EPA-600/2-85-106, September 1985.
[2] J. Irwin, "Estimating Plume Dispersion: A Comparison of Several Sigma Schemes," *J. Appl. Meteorol.*, vol. 22, no. 1, 1983.
[3] G. Briggs, "A Plume Rise Model Compared with Observations," *JAPCA*, no. 15, p. 433-438, 1965.
[4] U. E. P. Agency, "User's guidelines for EPA SCREEN3 and AERSCREEN dispersion model," [Online]. Available: http://www.epa.gov/ttn/scram/dispersion_screening.htm).
[5] M. McDaniel, "Flare Efficiency Study," Engineering-Science, Inc., (for EPA Contract 68-02-3541-6), Austin Tex., 1983.
[6] D. T. Allen and V. M. Tones, "TCEQ 2010 Flare Study Final Report," The University of Texas at Austin The Center for Energy and Environmental Resources, Austin, Tex., 2011.
[7] J. D. McEwen and M. R. Johnson, "Black carbon particulate matter emission factors for buoyancy-driven," *Journal of the Air & Waste Management Association*, 62:3, pp. 307-321, 2012.
[8] M. R. Johnson, R. W. Devillers and K. A. Thomson, "Quantitative Field Measurement of Soot Emission from a Large Gas Flare Using Sky-LOSA," *Environ. Sci. Technol.*, vol. 45, no. 1, pp. 345-350, 2011.
[9] M. R. Johnson, R. W. Devillers, C. Yang and K. A. Thomson, "Sky-Scattered Solar Radiation Based Plume Transmissivity Measurement to Quantify Soot Emissions from Flares," *Environ. Sci. Technol.*, vol. 44, no. 21, pp. 8196-8202, 2010.
[10] URS Corporation, "Passive FTIR Phase I Testing of Simulated and Controlled Flare Systems FINAL REPORT," URS Corporation, Houston, Tex., 2004.
[11] N. Ames, "Ames Technology Capabilities and Facilities," NASA, [Online]. Available: http://www.nasa.gov/centers/ames/research/technology-onepagers/gas_detection.html.
[12] D. B. G. Ilia N. Ivanov, "Carbon nanotube temperature and pressure sensors Mar. 3, 2011". US Patent US 20110051775 A1, 3 Mar. 2011.
[13] S. B. P. B. Michael S. Strano, "Sensors employing single-walled carbon nanotubes, Jul. 1, 2014". U.S. Pat. No. 8,765,488 B2, 1 Jul. 2014.
[14] C. LANDORF, "Highly soluble carbon nanotubes with enhanced conductivity". Patent WO 2012177975 A1, 27 Dec. 2012.

What is claimed is:

1. An air quality measurement system for a plurality of adjacent ground emission sources, which system comprises:
    a plurality of unmanned aerial vehicles operating aerially above and around a plurality of adjacent ground flares, wherein each of said plurality of adjacent ground flares includes an emission source, said emission sources of said plurality of adjacent ground flares together forming a complex flume;
    a plurality of electrically interconnected sensors mounted on each of said plurality of said unmanned aerial vehicles to monitor atmospheric gaseous emissions from said complex flume, said sensors having a gas sensitive electronically active sensing layer with a dielectric or metallic layered structure;
    wherein said plurality of sensors is configured to measure said gaseous emissions including CO, NOx, benzene, toluene, xylene, acrolein, formaldehyde, acetaldehyde, and acetonitrile; and
    a data collection central processing unit to collect and analyze data from said plurality of sensors on each of said plurality of unmanned aerial vehicles regarding said atmospheric properties; and
    a position controller central processing unit whereby the location of each of said plurality of unmanned aerial vehicles is controlled with respect to each other said plurality of unmanned aerial vehicles configured to operate together to sense said complex flume.

2. The air quality measurement system as set forth in claim 1 wherein location information on each said plurality of unmanned aerial vehicles is correlated with said atmospheric properties.

3. The air quality measurement system as set forth in claim 1 wherein said sensors monitor atmospheric temperature.

4. The air quality measurement system as set forth in claim 1 wherein said sensors monitor atmospheric relative humidity.

5. The air quality measurement system as set forth in claim 1 wherein said data regarding said atmospheric properties is analyzed as a function of time, location, and elevation.

6. The air quality measurement system as set forth in claim 1 including a communication transmission mechanism to transmit said data from said sensors on each of said unmanned vehicles to said data collection central processing unit.

7. The air quality measurement system as set forth in claim 1 wherein each of said plurality of unmanned aerial vehicles is constructed of high temperature glass-ceramic matrices which are temperature and chemical resistant.

8. The air quality measurement system as set forth in claim 1 wherein said plurality of adjacent ground emission sources is a multi-point ground flare array.

9. A method of measuring air quality, which method comprises:

acquiring multiple atmospheric air property measurements from multiple unmanned aerial vehicles, with a plurality of sensors mounted on each of said unmanned aerial vehicles, said sensors comprising a plurality of electrically interconnected sensors, each having a gas sensitive electronically active sensing layer with a dielectric or metallic layered structure wherein said plurality of sensors is configured to measure gaseous emissions including CO, NOx, benzene, toluene, xylene, acrolein, formaldehyde, acetaldehyde, and acetonitrile;

controlling and determining the location of each of said plurality of unmanned aerial vehicles with respect to each other with a position controller central processing unit configured to operate together to sense said complex flume;

transmitting said multiple atmospheric air measurements from a transmitter on each of said plurality of unmanned aerial vehicles; and receiving, collecting, and analyzing data from each said sensors of each of said unmanned aerial vehicles with respect to each other said plurality of unmanned aerial vehicles.

10. The method of measuring air quality as set forth in claim 9 wherein said multiple atmospheric air property measurements are taken from different locations at different elevations at different times.

11. The method of measuring air quality as set forth in claim 9 wherein said multiple atmospheric air property measurements include atmospheric pressure, atmospheric relative humidity and gaseous emissions.

12. The method of measuring air quality as set forth in claim 9 wherein said multiple atmospheric air property measurements are taken from multiple adjacent ground emission sources.

* * * * *